United States Patent [19]

Bonetti

[11] 4,012,443
[45] Mar. 15, 1977

[54] INTEGRATED UREA-AMMONIA PROCESS

[75] Inventor: Andrea Bonetti, San Donato Milanese, Italy

[73] Assignee: Snam Progetti S.p.A., Milan, Italy

[22] Filed: June 12, 1975

[21] Appl. No.: 586,359

[30] Foreign Application Priority Data

June 12, 1974 Italy .................................. 23895/74

[52] U.S. Cl. .............................. 260/555 A; 423/359
[51] Int. Cl.² .......................................... C07C 126/00
[58] Field of Search .......................... 423/220, 359; 260/555 A

[56] References Cited

UNITED STATES PATENTS

| | | | |
|---|---|---|---|
| 3,349,126 | 10/1967 | Hsu et al. | 260/555 A |
| 3,357,901 | 12/1967 | Otsuka et al. | 260/555 A |
| 3,436,317 | 4/1969 | Otsuka et al. | 260/555 A |
| 3,506,710 | 4/1970 | Inoue et al. | 260/555 A |
| 3,607,938 | 9/1971 | Braun | 260/555 A |
| 3,666,807 | 5/1972 | Yamagishi et al. | 260/555 A |
| 3,674,847 | 7/1972 | Kaiasenbrood et al. | 260/555 A |
| 3,684,442 | 8/1972 | Konori et al. | 260/555 A |
| 3,725,210 | 4/1973 | Otsuka et al. | 260/555 A |

*Primary Examiner*—G. O. Peters
*Assistant Examiner*—Eugene T. Wheelock
*Attorney, Agent, or Firm*—Ralph M. Watson

[57] ABSTRACT

Improved integrated process for simultaneous synthesis of ammonia and urea. Improved yields of urea in purified form are obtained by a simple process which curtails the addition of external water to the process. Two carbon dioxide absorbers are employed. A concentrated ammonium carbonate solution is utilized in the primary carbon dioxide absorber. A secondary carbon dioxide absorber is downstream in series to the first or primary carbon dioxide absorber. An ammonical solution of ammonium carbonate is utilized in the secondary carbon dioxide absorber.

1 Claim, 1 Drawing Figure

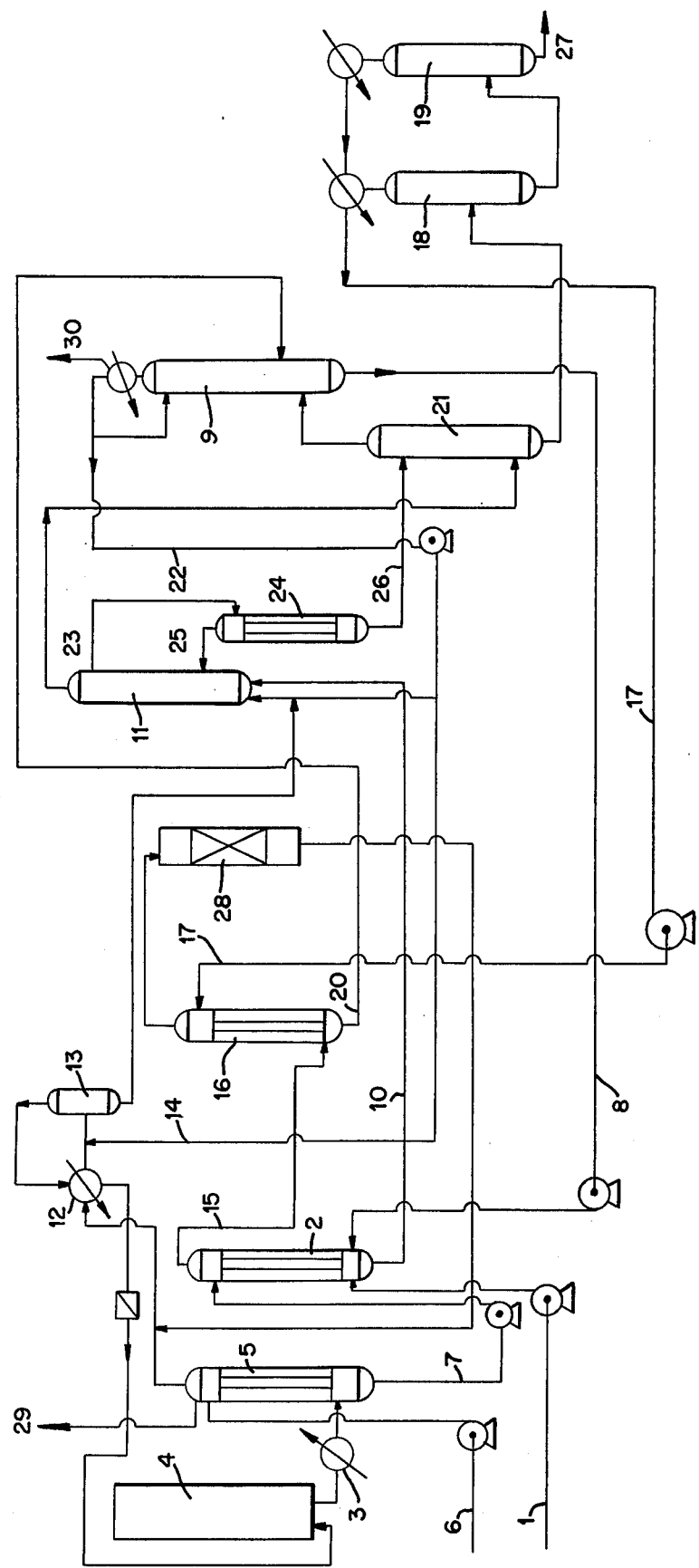

4,012,443

INTEGRATED UREA-AMMONIA PROCESS

BACKGROUND OF THE INVENTION

The present invention relates to an integrated process for the synthesis of urea and ammonia.

The integrated urea-ammonia processes in which $CO_2$ contained in the gaseous feed sent to the $NH_3$ synthesis is absorbed by aqueous ammoniacal solutions, can be described in the following manner.

The feed gas utilized in the synthesis of $NH_3$ contains $N_2$, $H_2$, $CO_2$ and small amounts of Ar, $CH_4$ and CO and is compressed to the ammonia synthesis pressure and fed to a primary absorber, wherein a selective absorption is carried out by means of an ammoniacal solutions obtained in various ways. In any case, the ammonia stream leaving the synthesis is utilized in order to remove $CO_2$ and to form ammonium carbamate.

The ammoniacal solution is fed to the absorber bottom and to the absorber top for increasing as much as possible the $CO_2$ absorption and for limiting, as much as possible, the evaporation of $NH_3$ due to heat developed during the carbamate formation.

Ammonium carbamate is subsequently sent to a urea synthesis zone wherein it is dehydrated, transforming partially into urea.

The urea-ammonium carbamate mixture which leaves the urea synthesis zone is fed to a stripping zone wherein by the action of heat the carbamate is transformed into $CO_2$ and $NH_3$ and by means of a stripping agent said compounds are recovered and sent back to the synthesis zone after, or without, previous condensation.

An aqueous solution of urea containing a small amount of carbamate is discharged from the stripping zone.

The pressure of the stripping zone for the urea solution is the same as that utilized in the formation of the carbamate and the synthesis of the urea. The pressure under which the urea solution is maintained is gradually decreased, generally in two stages, down to atmospheric pressure. At the first stage of lowered pressure (in general at about 16 atmospheres) the urea solution is distilled, obtaining as overhead products, water, ammonia and $CO_2$ which, after condensation-rectification in a single column, are separated into a gaseous phase constituted by $NH_3$ and a liquid phase constituted by a concentrated solution of ammonium carbonate which is sent back to the urea synthesis zone. The urea solution leaving the first distillation stage at the lowered pressure is fed to a second distillation stage at a further reduced pressure (in general at about 4 atmospheres) which separates as overhead products, ammonia, water and $CO_2$ which after condensation give a weakly concentrated ammoniacal solution of ammonium carbonate. This last solution in the continuation of the description will be referred to as "ammoniacal solution" is recycled to the condensation-rectification column in order to recover liquid ammonia and carbonate. The carbonate is recycled together with the previously mentioned carbonate to the urea synthesis zone.

From the chemical-physical data known from the literature and confirmed by the experimental values obtained with apparatus analogous that are used for industrial applications it is known that the residual amount of $CO_2$ in the gas leaving the absorber depends upon, in addition to the total pressure of the system, the composition of the obtained carbamate solution, the amount of $NH_3$ in excess of the stoichiometric value necessary to form carbamate present in the gaseous and liquid phases, the concentration of the absorbing solution, and the temperature of the liquid and gaseous phases.

Also, by utilizing as the $CO_2$ absorbing solution, the ammoniacal solution obtained by absorption of the $NH_3$ from the synthesis, or also the aqueous urea and the $NH_3$ solutions, the amount of residual $CO_2$ contained in the gas is still high. Because of this, the recovery of a portion, or all of the $NH_3$ contained therein by condensation by cooling is not possible. Because of this, the $NH_3$ remains in the gas, and before being eliminated by absorption, is fed to a subsequent stage of elimination of CO.

Said absorption can be carried out also in the previously described $NH_3$ absorption stage.

A drawback is presented in absorbing the evaporated ammonia because in order to do this an additional amount of water over and above that necessary to absorb the ammonia coming from the primary synthesis is required.

The final result is that the amount of water which is utilized at first in the absorption of $NH_3$, then in the absorption of $CO_2$, and at last together with carbamate in the synthesis of urea is particularly high. Because of this, the urea synthesis reaction, stripping and recovery of $CO_2$ and $NH_3$ not converted into urea, in the plant sections downstream of the stripper are remarkably influenced in a negative sense. There is in fact a lowering of the conversion of carbamate to urea, an increase of hydrolisis of urea in the stripping stage and in the subsequent distillation stages of the urea solution, an increase of steam consumed, of the amount of cooling water and energy required, and an increase of the cost of the apparatus constituting the plant, and so on.

SUMMARY OF THE INVENTION

It has been found, and this constitutes the object of the present invention, that it is possible to eliminate the aforesaid drawbacks concerning the $CO_2$ and $NH_3$ content of the gases leaving the absorption stage by utilizing the concentrated ammonium carbonate solution obtained from the first stage of distillation of the urea solution at low pressure and the "ammoniacal solution" obtained from the second stage of distillation of the urea solution at the lowest pressure. In addition, a remarkable advantage in increased yield of urea obtained in the process is achieved as well as significant advantages in reducing the costs of the process.

The process according to the present invention comprises feeding the concentrated ammonium carbonate solution, rather than directly to the urea reactor, to the $CO_2$ primary absorber and the "ammoniacal solution" to a secondary absorber at high pressure placed immediately downstream of the primary $CO_2$ absorber, and absorbing in the secondary absorber all of the $CO_2$ and $NH_3$ leaving the $CO_2$ primary absorber in the "ammoniacal solution", and then passing the "ammoniacal solution" following absorption of $NH_3$ and $CO_2$, to the bottom of the condensation-rectification column wherefrom concentrated ammonium carbamate is separated.

Advantages obtained by following the process of the present invention are as follows.

By feeding the concentrated ammonium carbonate solution to the $CO_2$ primary absorber the carbamate solution fed to the urea synthesis is more diluted and therefore there are fewer technological problems due to the possible formation of solid ammonium carbonate involved in transferring it to the reactor. Furthermore, in the $CO_2$ primary absorber, there is an increase of the amounts of water and ammonia (due to the concentrated carbonate solution) and therefore the $CO_2$ absorption is remarkably increased.

The sending of the concentrated carbonate solution to the absorber on the other hand, at last permits feeding the absorbing the ammoniacal solution in higher amounts to the top of the same absorber with consequent further lowering of the $CO_2$ content.

The "ammoniacal solution" fed to a secondary absorber downstream of the primary $CO_2$ absorber allows the total removal of $CO_2$ leaving the primary absorber and the total removal of the excess $NH_3$ leaving the same primary absorber, thus removing $NH_3$ (undesired compound) from the gases sent to the removal of CO.

This process also avoids the use of any additional amounts of water for the removal of the $NH_3$.

This decrease in the amount of absorbing water results in increased yields of urea or, if the yields of urea are kept equal, a reduction in the cost of the apparatus of the plant since the operations can be carried out under more moderate conditions of pressure and temperature, both for the absorption of $CO_2$ and for the conversion of carbamate to urea.

The "ammoniacal solution", after absorption of $NH_3$ and $CO_2$, is sent to the condensation-rectification stage for the gases coming from the first distillation at low pressure, allowing the condensation of said gases and, utilizing the condensation heat, the evaporation of $NH_3$, which is recovered in liquid form. The ammonia thus may be utilized again in the plant.

In conventional processes, the condensation-rectification was effected by refluxing to the column the liquid ammonia, separated as overhead product by the heat of condensation from the gases obtained from the distillation.

Liquid ammonia evaporated and was then subsequently condensed and used again as above described. The amount of ammonia recovered as overhead product was considerably lower.

DESCRIPTION OF THE PREFERRED EMBODIMENT

The process of the present invention will now be described with reference to the accompanying drawing. The embodiment described is illustrative of the invention but in no way is to be considered restrictive of the invention which is defined in the accompanying claims.

Raw gases for the synthesis of ammonia which are constituted by $N_2$, $H_2$, $CO_2$, Ar, $CH_4$ and CO are fed through pipe 1 to the $CO_2$ primary absorber 2. At the top of the primary $CO_2$ absorber 2 a concentrated ammoniacal solution 7 is fed which is obtained by scrubbing ammonia in absorber indicated at 5. The ammonia in line 3 which is scrubbed in absorber 5 is fed to the absorber 5 from the ammonia synthesis apparatus 4. The water from line 6 is added to the absorber 5 as shown. The concentrated ammonical solution 7 from absorber 5 is fed to the top of the primary absorber 2 as shown in the accompanying diagram. A vent for the inert gases is shown at 29, leaving the ammonia synthesis apparatus 4 with water fed through 6.

A concentrated ammonium carbonate solution 8 coming from the stage 9 at a pressure of 16 ata is fed to the bottom of the primary absorber 2.

The ammonium carbamate solution which is discharged from the bottom of the primary absorber 2 is fed through pipe 10 to the apparatus 11 for the synthesis of urea.

Gases leaving absorber 5 constituted by $N_2$, $H_2$, Ar, $CH_4$ and CO are dehydrated by cooling in 12 and subsequent injection of liquid ammonia 14. After that, in 13 the separation of the dehydrated gases is effected. The dehydrated gases are then recycled to the ammonia synthesis reactor 4 after passing through the exchanger 12 following separation in 13. Concentrated ammonia solution obtained as indicated at the bottom of 13 is fed from 13 to the urea synthesis reactor 11 as shown where it is added to the ammonia obtained from the top of column 9 in the manner described.

The gaseous mixture leaving the $CO_2$ primary absorber 2 is fed through pipe 15 to a secondary absorber 16 wherein it meets in countercurrent the weakly concentrated ammoniacal solution of ammonium carbonate 17 obtained in the stages 18 and 19.

The solution 20 of ammonia 20 leaving the secondary absorber 16 is fed to column 9 in order to condensate $NH_3$, $CO_2$ and water coming from distillation column 21 forming the concentrated ammonium carbonate solution 8 which is fed at a pressure 16 atmospheres to the bottom of primary absorber 2 as described above.

The ammonia contained in solution 20 is liberated by the heat of formation of ammonium carbonate formed by the condensation of the gases leaving the top of distillation column 21. The ammonia is discharged as the overhead product from column 9.

The ammonia from column 9 in the liquid state is fed to the urea synthesis reactor 11 through line 22 and to the dehydration of the gases to be recycled to the synthesis of ammonia through line 14.

The gaseous stream leaving the top of the secondary absorber 16 is passed through the methanation apparatus 28 wherein CO is removed and then joined to the stream leaving the top of absorber 5 so that it can be dehydrated together with said stream.

From the urea synthesis reactor 11 a stream 23 is discharged which is fed to stripper 24 wherein carbamate which has not been converted to urea is decomposed, obtaining $CO_2$ and $NH_3$ which are recycled through 25 and an urea solution containing a small amount of carbamate. The urea solution containing the carbamate is fed through 26 to the distillation apparatus 21 at 16 ata. As indicated previously, in the distillation apparatus 21, there is obtained as overhead products $NH_3$, $CO_2$ and $H_2O$ which are then condensed in column 9 to form the concentrated ammonium carbonate solution. The bottom product of the distillation apparatus 21 is the urea solution which is then further distilled in distillation columns 18 and 19. A urea solution free from all undesired components is obtained as shown at 27.

Inert gases and small amounts of $CO_2$ and $NH_3$ discharged from the top of the urea synthesis column 11 are recycled to the distillation columm 21 as shown in the accompanying drawing. A vent 30 for inert gases is shown at the top of column 9.

What we claim is:

1. An integrated process for the synthesis of urea and ammonia comprising:

a. feeding raw gases comprising $N_2$, $H_2$ and $CO_2$ Ar, $CH_4$ and CO to a primary $CO_2$ absorption zone wherein said gases are contacted with a concentrated ammonical solution and said $CO_2$ is removed to form an ammonium carbamate solution which separates from said raw gases but still contains an amount of $CO_2$ and $NH_3$, said concentrated ammonical solution having been obtained by absorbing with water the ammonia from the ammonia synthesis of step (n);

b. feeding said ammonium carbamate solution thus obtained to a urea synthesis zone for transforming said ammonium carbamate into urea;

c. forming said urea in said urea synthesis zone;

d. discharging from said urea synthesis zone a solution comprising urea, non-transformed carbamate, water, and ammonia to a stripping zone maintained at the same pressure as that of said urea synthesis zone;

e. obtaining from said stripping zone as the overhead products the decomposition products $CO_2$ and $NH_3$ of ammonium carbamate; then f. feeding said decomposition products back to said urea synthesis zone; and g. obtaining as the bottom product of said stripping zone in (e) an aqueous urea solution containing ammonia and non-transformed carbamate;

h. feeding said aqueous urea solution to a first distillation stage at a lowered pressure;

i. separating as overhead products of said first distillation stage water, $NH_3$ and $CO_2$, which water, $NH_3$ and $CO_2$, following condensation and rectification, are separated into:
  i. a concentrated ammonium carbonate solution;
  ii. liquid ammonia; and j. obtaining as the bottom product of the distillation stage of (h) a urea solution;

k. distilling said urea solution of (j) in a second distillation stage at a still lower pressure and thereby obtaining a substantially pure urea solution product;

l. recovering as the overhead product of said second distillation stage after condensation a weakly concentrated ammonical solution of ammonium carbonate;

m. feeding said concentrated ammonium carbonate solution to said primary $CO_2$ absorption zone;

n. feeding said weakly concentrated ammonical solution of ammonium carbonate obtained in step (l) to a secondary $CO_2$ absorption zone so as to contact therein the raw gas stream comprising $N_2$, $H_2$, Ar, $CH_4$, CO and unabsorbed $CO_2$ and $NH_3$ treated in step (a) and further synthesizing ammonia from said treated gas stream;

o. feeding an ammonium carbonate solution obtained from the secondary $CO_2$ absorber to a condensation-rectification stage to which are added $NH_3$, $CO_2$ and water obtained as the overhead products from said first distillation stage at said lowered pressure;

p. obtaining from said condensation-rectification stage simultaneously
  i. as the overhead product, liquid ammonia; and
  ii. as the bottom product, said concentrated ammonium carbonate solution;

q. said liquid ammonia being recycled to said urea synthesis zone.

* * * * *